US00PP23870P2

(12) United States Plant Patent
van Zoest

(10) Patent No.: US PP23,870 P2
(45) Date of Patent: Sep. 3, 2013

(54) *CLEMATIS* PLANT NAMED 'ZOBAST'

(50) Latin Name: ***Clematis* hybrid**
Varietal Denomination: Zobast

(75) Inventor: Jan van Zoest, Boskoop (NL)

(73) Assignee: J. van Zoest Beheer B.V., Boskoop (NL)

( * ) Notice: Subject to any disclaimer, the term of this patent is extended or adjusted under 35 U.S.C. 154(b) by 77 days.

(21) Appl. No.: 13/385,272

(22) Filed: Feb. 10, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Penny J. Aguirre

(57) ABSTRACT

A new cultivar of hybrid *Clematis*, 'Zobast', characterized by its upright, star-shaped, single to occasionally double flowers that are white in color, its ability to bloom in spring and even more abundantly in summer, its near sterility, and its cold hardiness to at least U.S.D.A. Zone 6.

2 Drawing Sheets

Botanical classification: *Clematis* hybrid.
Variety denomination: 'Zobast'.

CROSS REFERENCE TO A RELATED APPLICATION

This application is co-pending with a U.S. Plant Patent Application filed for a plant derived from similar parentage that is entitled *Clematis* Plant Named 'Zobadol' (U.S. Plant patent application Ser. No. 13/385,252).

BACKGROUND OF THE INVENTION

The present invention relates to a new and distinct cultivar of *Clematis*, botanically an interspecific hybrid (Patens group), and will be referred to hereafter by its cultivar name 'Zobast'. 'Zobast' is grown as an herbaceous climbing plant for use in the landscape or as a flowering potted plant for the terrace.

'Zobast' derived from an ongoing breeding program by the inventor in his nursery in Boskoop, The Netherlands. The goal of the selection was to select a cold hardy climber with a dwarf habitus that could be grown for different purposes in the garden.

'Zobast' arose as a seedling derived from open pollination of an unnamed plant from the breeding program, designated as No. 19960074 in 2003. 'Zobast' was selected as a single unique plant from the batch of seedlings in 2006.

Asexual reproduction of the new cultivar was first accomplished by internodial stem cuttings under the direction of the Inventor in Boskoop, The Netherlands in 2006. The characteristics of this cultivar have been determined to be stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zobast' from other varieties of *Clematis* known to the Inventor.

1. 'Zobast' exhibits upright flowers that are white in color.
2. 'Zobast' blooms in spring and even more abundantly in summer.
3. 'Zobast' exhibits flowers that are star-shaped, they are typically single but the first flowers may be double in spring (double flowers stand solitary and terminal on the shoot).
4. 'Zobast' is more or less sterile; seed is barely produced.
5. 'Zobast' is cold hardy to at least U.S.D.A. Zone 6.

'Zobast' differs from its female parent, No. 19960074, in having white flowers rather then violet-blue, and in having a much more floriferous habitus. 'Zobadol' differs from 'Zobast' in having light violet flowers and in only having single flowers.

'Zobast' can be most closely compared to the cultivars 'Huldine' (not patented) and 'The Bride' (not patented), differences are described in TABLE 1.

TABLE 1

| | Characteristic | Comparison cultivar | 'Zobast' |
|---|---|---|---|
| 'Huldine' | Tepal shape | Oblong with obtuse apex | Ovate with acute apex |
| 'Huldine' | Tepal color at lower surface | White with pink centers | White with white centers |
| 'The Bride' | Tepal shape | Broadly ovate with obtuse apex | Ovate with acute apex |
| 'The Bride' | Flower shape | Always single | First flowers may be double |

BRIEF DESCRIPTION OF THE DRAWING

The accompanying colored photographs illustrate the overall appearance and distinct characteristics of the new *Clematis*. The photographs were taken of three year-old plants of 'Zobast' as grown in one-gallon containers in Boskoop, The Netherlands.

The photograph in FIG. 1 shows the flowering habitus.

Figure 1:
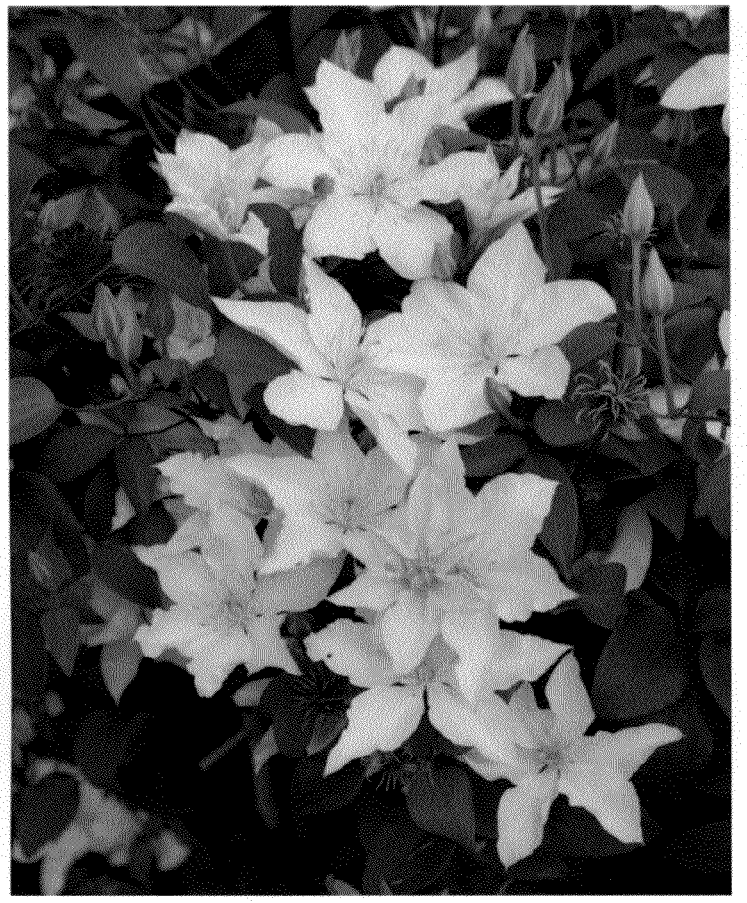
Figure 2:
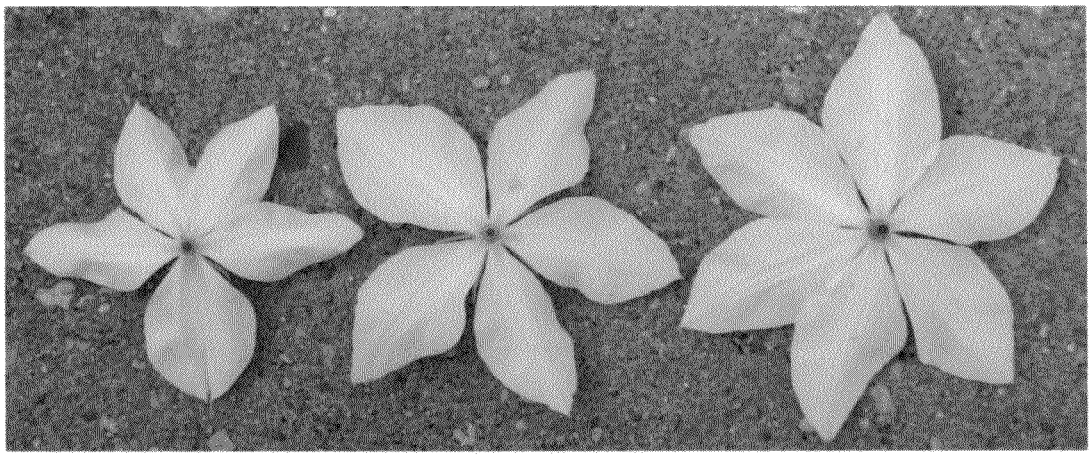

The photograph in FIG. 2 shows the back of the flower.

Figure 3:
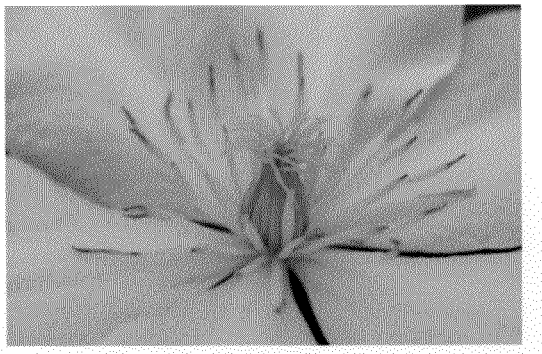

The photograph in FIG. 3 shows the inside of the flower with a close up of the stamens and pistils.

Figure 4:
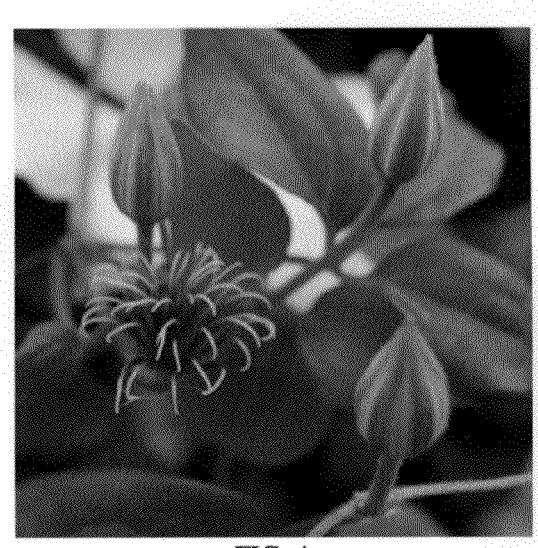

The photograph in FIG. 4 shows the flower buds.

Figure 5:
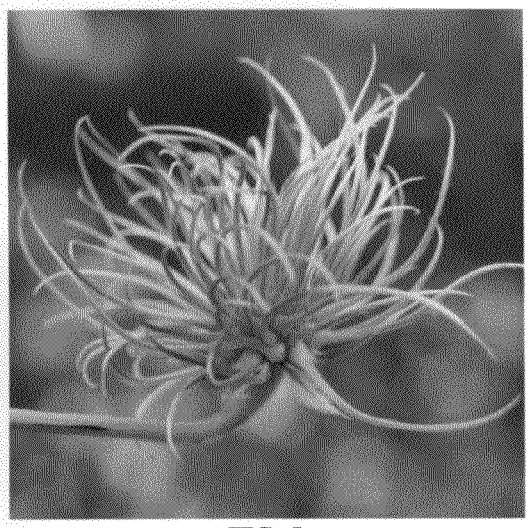

The photograph in FIG. 5 shows the seedhead.

Figure 6:
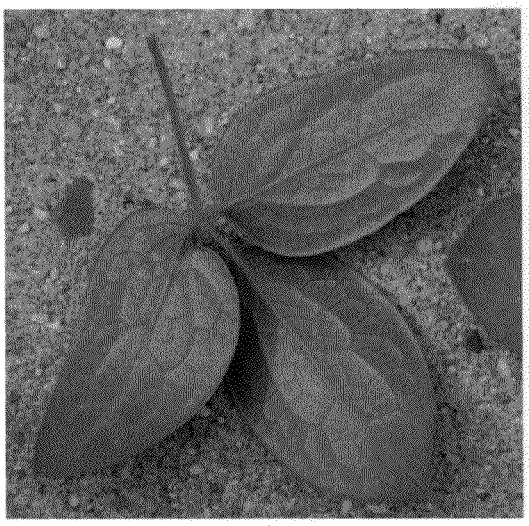
Figure 7:
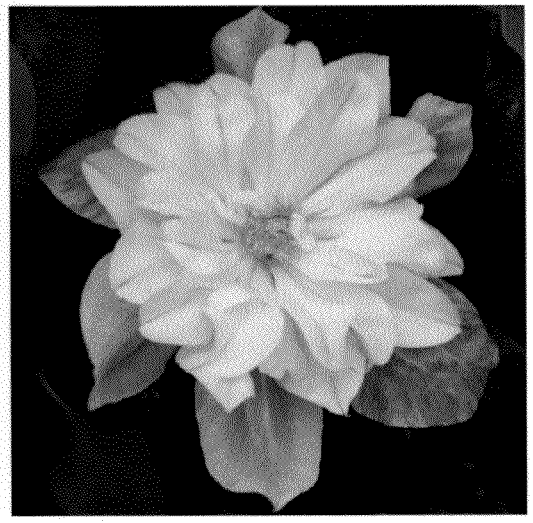

The photograph in FIG. 6 shows the lower surface of the leaves and the photograph in FIG. 7 shows a double flower.

The colors of the photographs are as close as possible with the digital photography techniques available, the color values cited in the detailed botanical description describe the colors as accurately as possible of the new *Clematis*.

DETAILED BOTANICAL DESCRIPTION

The following is a detailed description of three year-old plants of *Clematis* 'Zobast' as grown outdoors in one-gallon containers under full sun at a nursery in Boskoop, The Netherlands. The phenotype of the new cultivar of *Clematis* may vary with variations in environmental, climatic and cultural conditions as the cultivar has not been tested under all possible environmental conditions. The color determination is in accordance with The 2001 R.H.S. Colour Chart, London, England, except where general color terms of ordinary dictionary significance are used.

General description:

*Botanical classification.*—*Clematis* 'Zobast' (classified in the Patens Group).

*Blooming period.*—Blooms for 4 to 6 weeks in spring and more abundantly in summer for 6 to 8 weeks.

*Plant habit.*—Herbaceous climber.

*Height and spread.*—Three year-old plant is about 15 cm at the base with a height of about 1.5 m height when pruned after the first flowering.

*Cold hardiness.*—At least to U.S.D.A. Zone 6.

*Culture.*—Moist but well-drained soil in full sun with the roots shaded.

*Diseases and pests.*—No resistance to wilt had been observed.

*Root description.*—Fleshy.

Growth and propagation:

*Propagation.*—Internodial soft wood cuttings from vegatative shoots.

*Root initiation.*—Roots develop in 6 weeks in summer under greenhouse conditions.

*Time required for root development.*—75 to 90 days to develop a 5-cm container from a 5-cm cutting.

*Growth rate.*—Moderately vigorous once planted out.

Stem description:

*Shape.*—Round and 6-ribbed.

*Stem color.*—N77A.

*Stem size.*—About 1.5 m (including peduncle and terminal pedicel) in length, an average of 2 to 3 mm in diameter.

*Stem surface.*—Covered in sparse short hairs but more densely so near the nodes.

*Internode length.*—Ranges from 4 to 6 cm.

*Branching.*—Basal branches.

Foliage description:

*Leaf arrangement.*—Opposite.

*Leaf division.*—Ternate.

*Leaf size.*—Up to 10 cm long and 7 cm in width.

*Leaf attachment.*—Petiolate.

*Leaflet shape.*—Elliptic.

*Leaflet base.*—Obtuse.

*Leaflet apex.*—Acute.

*Leaflet fragrance.*—Fresh "green" fragrance when crushed.

*Leaflet venation.*—Just slightly reticulate at upper surface, lower surface slightly reticulate.

*Leaflet margins.*—Entire.

*Leaflet attachment.*—Petiolulate.

*Leaflet surface.*—Upper surface glabrous with a few hairs on the main veins; lower surface sparsely hairy with main veins more densely so.

*Leaflet size.*—Up to 5.5 cm in length and up to 3 cm in width.

*Leaflet color.*—Upper surface 147A, lower surface 147B.

*Petioles and petiolules.*—Petiole up to 4 cm in length and about 3 mm in width, 146B in color, sparsely hairy; petiolule 0.7 to 1.2 cm in length and about 2 mm in width, 146B in color, surface is a bit articulate and sparsely hairy on both.

Inflorescence description:

*Inflorescence type.*—Solitary or 3-flowered dichasial cyme.

*Inflorescence arrangement.*—Terminal and axillary on young shoots.

*Peduncles.*—3 to 4 cm in length, 144A in color and may be suffused with 187A, round and just slightly 6 ribbed in shape, surface covered in sparse short hairs.

*Pedicels.*—3 to 5 cm in length, 144A in color, round in shape, surface covered in sparse short hairs.

*Peduncle bracts.*—Leaf-like but simple.

*Flower bud description.*—Held upright, ovate at first but later lanceolate in shape, 144B in color with seams 155B and slight bit of 59B at the apex, apex acuminate, base obtuse, surface covered in sparse short hairs with very short hairs on seams.

*Flower fragrance.*—None.

*Lastingness of the flowers.*—Individual flowers last up to about 10 days until the first tepal drop followed later by the stamens.

*Flower quantity.*—Solitary flowers or in a 3-flowered dichasial cyme, terminal and axillary on young shoots, about 30 to 50 flowers in spring and 50 to 70 flowers in summer on a 3 year old plant.

*Flower type.*—Spreading, single but on an established plant the first flowers might be double (in which case they are solitary on terminal).

*Flower aspect.*—Upright facing.

*Flower size.*—Range from 5 to 8 cm in diameter and about 3 cm in depth.

*Flower sex.*—Bisexual.

*Tepal number.*—Usually 5 or 6 in number but sometimes 4 on single flowers, an average of 22 on double flowers (including staminodes that are similar to characteristics to tepals).

*Tepal shape.*—Elliptic.

*Tepal apex.*—Acute.

*Tepal base.*—Cuneate.

*Tepal margin.*—Entire.

*Tepal surface.*—Upper surface; glabrous, lower surface; hairy, margin glabrous but heavily covered in short hairs towards middle.

*Tepal color.*—Upper surface; whiter than 155A with a occasional marking of 157A, especially near base and on midrib; lower surface 155A with small lines in midrib of 157A extending to base.

*Tepal and staminode size.*—Up to 4 cm in length and 2.5 cm in width.

Reproductive organs:

*Gynoecium.*—Numerous pistils (about 30 to 40), 1.2 cm in length, style a blend of 155A and 145D, ovary 144B, stigma 158B, rather thin and slightly reflexed.

*Androcoecium.*—Filaments are 0.4 to 1 cm in length and 1 mm in width, linear, 155B in color, glabrous surface, anthers; 4 mm in length, linear, 155A; connective not elongated, 155A becoming 202A; in spring flowers some tepal-like staminodes which gives the appearance of a double flower, whiter than 155A in color with midrib 144B on upper and lower surface, apex acute to emarginated, similar in characteristics to tepals.

*Seed.*—Head; to 5 cm in diameter, style; up to 3 cm in length, 144C in color with hairs 161C, ovary; 144B in color with a hairy surface, stigma; 145B in color, just a bit bent to almost straight with tip 161B in color, seed; more or less sterile; seed is barely produced.

It is claimed:

1. A new and distinct cultivar of *Clematis* plant named 'Zobast' as herein illustrated and described.

* * * * *